(12) United States Patent
Belshaw et al.

(10) Patent No.: US 7,183,406 B2
(45) Date of Patent: Feb. 27, 2007

(54) METHOD FOR THE SYNTHESIS OF DNA SEQUENCES

(75) Inventors: Peter J Belshaw, Madison, WI (US); Michael J. Sussman, Madison, WI (US); Francesco Cerrina, Madison, WI (US); Shane T. Flickinger, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/152,046

(22) Filed: May 20, 2002

(65) Prior Publication Data

US 2003/0068633 A1    Apr. 10, 2003

Related U.S. Application Data

(60) Provisional application No. 60/292,160, filed on May 18, 2001.

(51) Int. Cl.
*C07H 21/00* (2006.01)
*C12Q 1/68* (2006.01)

(52) U.S. Cl. .......................................... 536/25.3; 435/6
(58) Field of Classification Search ............. 435/287.2, 435/6; 702/20, 19; 536/24.3, 25.3
See application file for complete search history.

(56) References Cited

U.S. PATENT DOCUMENTS

| | | | |
|---|---|---|---|
| 5,571,639 A | 11/1996 | Hubbell et al. | |
| 6,074,708 A | 6/2000 | Onishi et al. | |
| 6,117,679 A | 9/2000 | Stemmer | |
| 6,218,530 B1 | 4/2001 | Rothschild et al. | |
| 6,368,861 B1 | 4/2002 | Crameri et al. | |
| 6,586,211 B1 | 7/2003 | Sthler et al. | |
| 6,600,031 B1 | 7/2003 | Fodor et al. | |

FOREIGN PATENT DOCUMENTS

| | | |
|---|---|---|
| WO | WO 99/42813 | 8/1999 |
| WO | WO 03/072832 A1 | 9/2003 |
| WO | WO 03/083053 A2 | 10/2003 |

OTHER PUBLICATIONS

Dubiley et al., Nucleic Acids Research, vol. 25, pp. 2259-2265, 1997.*
Peak et al., Analytical Biochemistry, vol. 169, pp. 189-193, 1988.*
Sing-Gasson et al., Nature Biotechnology, vol. 17, pp. 974-978, 1999.*
Merriam-Webster Online, "Overlap", www.m-w.com/cgi-bin/dictionary?book+Dictionary&va=overlapping, last visited Jan. 12, 2006.*
"Sequencing Whole Genomes," www.bio.davidson.edu/courses/genomics/method/shotgun.html, last visited Jan. 12, 2006.*
Beier et al., "Versatile derivatisation of solid support media for covalent bonding on DNA-microchips," *Nucleic Acids Research* 27:1970-1977 (1999).
Beier et al., "Analysis of DNA-microarrays produced by inverse in situ oligonucleotide synthesis," *Journal of Biotechnology* 94 15-22 (2002).
Kneidinger et al., "Scaling Up the Ligase Chain Reaction-Based Approach to Gene Synthesis," *Biotechniques* 30:249-252 (2001).
Au, et al., "Gene Synthesis by a LCR-Based Approach: High-Level production of Leptin-L54 Using Synthetic Gene in *Escherichia coli*," *Biochemical and Biophysical Research Communications* 248:200-203 (1998).
Beir, M., et al., "Production by quantitative photolithographic synthesis of individually quality checked DNA microarrays," Nucleic Acids Research 28:e11i-e11vi (2000).
Blanc, A., et al., "Wavelength-Controlled Orthogonal Photolysis of Protecting Groups," J. Org. Chem. 67:5567-5577 (2002).
Pirrung, M.C., et al., "3'-Nitrophenylpropyloxycarbonyl (NPPOC) Protecting Groups for High-Fidenity Automated 5'-3' Photochemical DNA Synthesis," Organic Letters 3:1105-1108 (2001).
Pon, R.T., et al., "Linker phosphoramidite reagents for oligonucleotide synthesis on underivatized solid-phase supports," Tetrahedron Letters 42:8943-8946 (2001).

(Continued)

*Primary Examiner*—Michael Borin
*Assistant Examiner*—Jerry Lin
(74) *Attorney, Agent, or Firm*—Quarles & Brady LLP

(57) ABSTRACT

A method is disclosed for the direct synthesis of double stranded DNA molecules of a variety of sizes and with any desired sequence. The DNA molecule to be synthesis is logically broken up into smaller overlapping DNA segments. A maskless microarray synthesizer is used to make a DNA microarray on a substrate in which each element or feature of the array is populated by DNA of a one of the overlapping DNA segments. The DNA segments are released from the substrate and held under conditions favoring hybridization of DNA, under which conditions the segments will spontaneously hybridize together to form the desired DNA construct. This method makes possible the remote assembly of DNA sequence, through a process analogous to facsimile transmission of documents, since the information on DNA to be made can be transmitted remotely to an instrument which can then synthesize any needed DNA sequence from the information.

9 Claims, 8 Drawing Sheets

OTHER PUBLICATIONS

Richmond, K.E., et al., "Amplification and assembly of chip-eluted DNA (AACED): a method for high-throughput gene synthesis," Nucleic Acids Research 32:5011-5018 (2004).

Shaginian, A., et al., "Light-Directed Radial Combinatorial Chemistry: Orthogonal Safety-Catch Protecting Groups for the Synthesis of Small Molecule Microarrays," J. Am. Chem. Soc. 126:16704-16705 (2004).

Singh-Gasson, S., et al., "Maskless fabrication of light-directed oligonucleotide microarrays using a digital micromirror array," Nature Biotechnology 17:974-978 (1999).

Stemmer, W.P.C., et al., "Single-step assembly of a gene and entire plasmid from large numbers of oligodeoxyribonucleotides," Gene 164:49-53 (1995).

* cited by examiner

Scheme 1: Preparation of MeNPOC protected diamine spacer (1) and 3'-hydrogen succinates of 5'-MeNPOC nucleosides (2) for use in preparation of nucleotide derivatized glass slides.

Scheme 2: Surface chemistry for attachment of 3' nucleotide to glass slide with a cleavable linker.

METHOD FOR THE SYNTHESIS OF DNA SEQUENCES

CROSS REFERENCE TO RELATED APPLICATION

This application claims the benefit of U.S. Provisional Application No. 60/292,160 filed May 18, 2001.

STATEMENT REGARDING FEDERALLY SPONSORED RESEARCH OR DEVELOPMENT

To be determined.

BACKGROUND OF THE INVENTION

This invention pertains generally to the field of biology and particularly to techniques and apparatus for the manufacture of DNA molecules of defined or desired sequences. The manufacture of DNA molecules also makes possible the synthesis of any desired peptides, proteins or assemblies of proteins and nucleic acids as may be desired.

Using the techniques of recombinant DNA chemistry, it is now common for DNA sequences to be replicated and amplified from nature and for those sequences to then be disassembled into component parts which are then recombined or reassembled into new DNA sequences. While it is now both possible and common for short DNA sequences, referred to a oligonucleotides, to be directly synthesized from individual nucleosides, it has been thought to be generally impractical to directly construct large segments or assemblies of DNA sequences larger than about 400 base pairs. As a consequence, larger segments of DNA are generally constructed from component parts and segments which can be purchased, cloned or synthesized individually and then assembled into the DNA molecule desired.

For example, if an expression vector is desired to express a new protein in a selected host, the scientist can often purchase a generic expression vector from a molecular biology supply company and then clone or synthesize the protein coding region for the gene sought to be expressed. The coding region must be ligated into the vector in such a manner and in the correct location and orientation such that the vector will be effective to express the desired protein in the host. The purchaser of the vector must also examine the sequence of the vector to make sure no other DNA component of the vector has other properties that might be detrimental to the experiment the purchaser wishes to run. Thus, the difficulty in constructing any new desired larger DNA construct is dependent on what similar constructs, or what components of the construct, can be purchased or obtained from public sources, and how much information is available about the sequences of those components.

Tools for genetic analysis are being developed to provide mechanisms to answer questions like these. Among such useful tools are what has become known as a DNA microarray. A DNA microarray is an array of different DNA strands arranged in an orderly fashion on a substrate. The DNA strands are organized into groups on the substrate, each individual group being called a feature. Ideally, all of the DNA strands in a single feature are identical in DNA sequence, and each of the different features can have an independent set of DNA strands of a different sequence from those in other features. It is a chemical trait of DNA that when single stranded DNA molecules are in solutions together at moderate or low temperatures, DNA strands of complementary sequence will spontaneously hybridize together through the formation of hydrogen bonds to form double stranded DNA. Thus a DNA microarray can be used to analyze a sample of unknown DNA (which has been made single stranded) to determine if complementary sequences are present in the sample simply by washing the unknown DNA sample over a microarray, and looking for the presence of double stranded DNA. DNA from the sample will hybridize to the array only when the sequence of the DNA from the sample matches the sequence in that particular feature. Thus, by intelligently designing and constructing DNA microarrays, which can contain thousands of these features in a single array, it becomes possible to rapidly gather large amounts of information about the DNA contained in a sample in a simple process. DNA microarrays are currently used mainly, and perhaps exclusively, for analytical purposes. Microarrays of DNA can be used for DNA sequencing, for the analysis of DNA from tissue samples, to identify individuals or to diagnose disease conditions and to study the tissue specific expression of native genes in any host.

To make a microarray of DNA strands, one can make a series of DNA strands and then place them on a support, or one can build DNA strands in situ covalently attached to the support. Both of these techniques have been used in the art to make microarrays. The first technique, sometimes referred to as spotting or gridding, is convenient for the rapid and convenient creation of novel or small quantity custom arrays since the capital cost of making the DNA strands is not large. The spotting strategy can, however, be limited in the density of the array that can be created due to the physical limitations of droplets of liquids containing DNA that can be deposited on a surface. The spotting strategy can also be error prone because of the need to keep strictly separate and properly identified hundreds or thousands of different oligonucleotides. The strategy of creating DNA strands in situ on a surface permits the manufacture of arrays in which each feature of the array is very small and in which there are very many features in a single array. Depending on the technique by which the DNA strands in the array are synthesized, however, the costs of making customized arrays can be quite high.

A technique has been described for the in situ synthesis of DNA microarrays that is adapted for the manufacturing of customized arrays. Published PCT patent application WO99/42813 and U.S. Pat. No. 6,375,903 describe a method for making such arrays in which the light is selectively directed to the array being synthesized by a high density micromirror array under software control from a computer. Since the micromirror array is operated totally under software control, the making of complex and expensive photolithographic masks is avoided in its entirety.

BRIEF SUMMARY OF THE INVENTION

The present invention is summarized in a method for constructing a DNA construct of defined sequence. The method begins with breaking up the sequence into a plurality of overlapping DNA segments using computer software. A DNA microarray is then made on a substrate in such a way that each single stranded probe on the array is constructed to be one of the overlapping DNA segments needed to make up the desired DNA construct. Then the probes are all released from the substrate. The probes will then self assemble into the desired DNA construct.

This invention makes possible the construction to order of DNA constructs of virtually any size. This frees the experimenter who wishes to perform experiments on DNA or on gene expression from the constraints of working with commercially available vectors or genetic elements. Instead, DNA sequences can be invented on a computer and fabricated for the first time and in a short time period using this microarray based technique.

This invention also makes possible the rapid re-embodiment of DNA information into physical DNA strands. Since DNA information can already be sent electronically to any desired location, the capacity to directly manufacture DNA of desired sequence makes it possible to send DNA to a remote location by a process analogous to facsimile transmission of a document.

Further objects, features and advantages of the invention will be apparent from the following detailed description when taken in conjunction with the accompanying drawings.

DETAILED DESCRIPTION OF THE INVENTION

The concept of the present invention is to use a microarray synthesizing instrument for the direct fabrication of DNA molecules of any desired sequence and of indefinite length. Sections or segments of the desired DNA molecule are fabricated in a massively parallel DNA synthesis process using the maskless array synthesizer instrument. After the synthesis of the segments, the segments are assembled to make the desired molecule. Some purification or isolation of the desired assembled DNA molecule may be required. In essence the technique described here permits the quick easy and direct synthesis of DNA molecule for any purpose in a simple and quick synthesis process.

Figure 1A:
FIGS. 1A, 1B, and 1C taken together are a simplified illustration of an example DNA molecule to be synthesized.
Figure 1B:
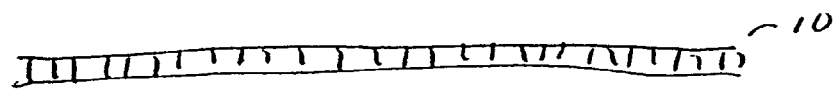
Figure 1C:
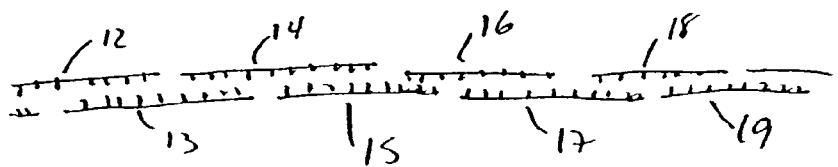

The invention can best be understood by illustrating the direct fabrication of a relatively simple DNA molecule. In FIG. 1, at 10, a double stranded DNA molecule of known sequence is illustrated. That same molecule is illustrated in both the familiar double helix shape in FIG. 1A, as well as in an untwisted double stranded linear shape shown in FIG. 1B. Assume, for purposes of this illustration, that the DNA molecule is broken up into a series of overlapping single smaller stranded DNA molecule segments, indicated by the reference numerals 12 through 19 in FIG. 1C. The even numbered segments are on one strand of the DNA molecule, while the odd numbered segments form the opposing complementary strand of the DNA molecule. The single stranded molecule segments can be of any reasonable length, but can be conveniently all of the same length which, for purposes of this example, might be 24 base pairs in length. Since the sequence of the molecule 10 of FIG. 1A is known, the sequence of the smaller DNA segments 12 through 19 can be defined simply be breaking the larger sequence into overlapping sequences each of 24 base pairs. In the normal nomenclature of the art, the DNA sequences on the microarray are sometimes referred to as probes because of the intended use of the DNA sequences to probe biological samples. Here these same sequences are referred to as DNA segments, also because of the intended use of these sequences.

Figure 2:
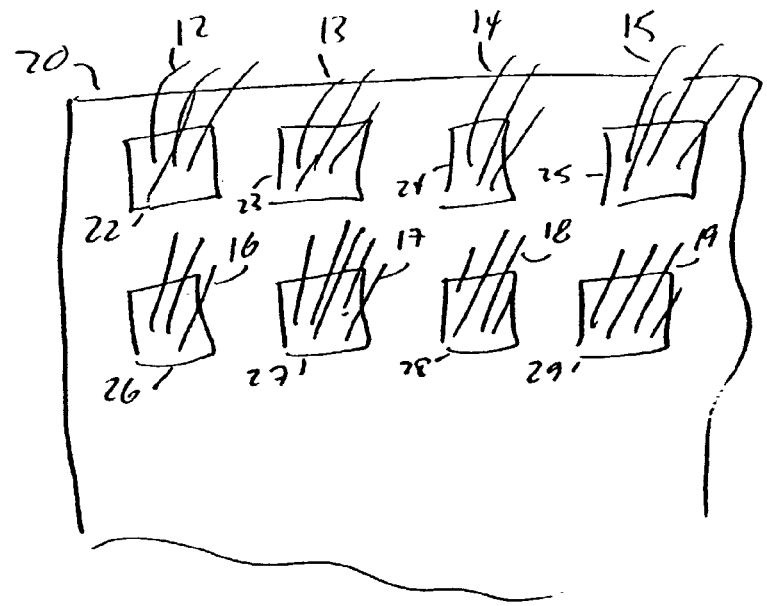
FIG. 2 illustrates a microarray used in the synthesis of the exemplary DNA molecule of FIG. 1.
Figure 3:
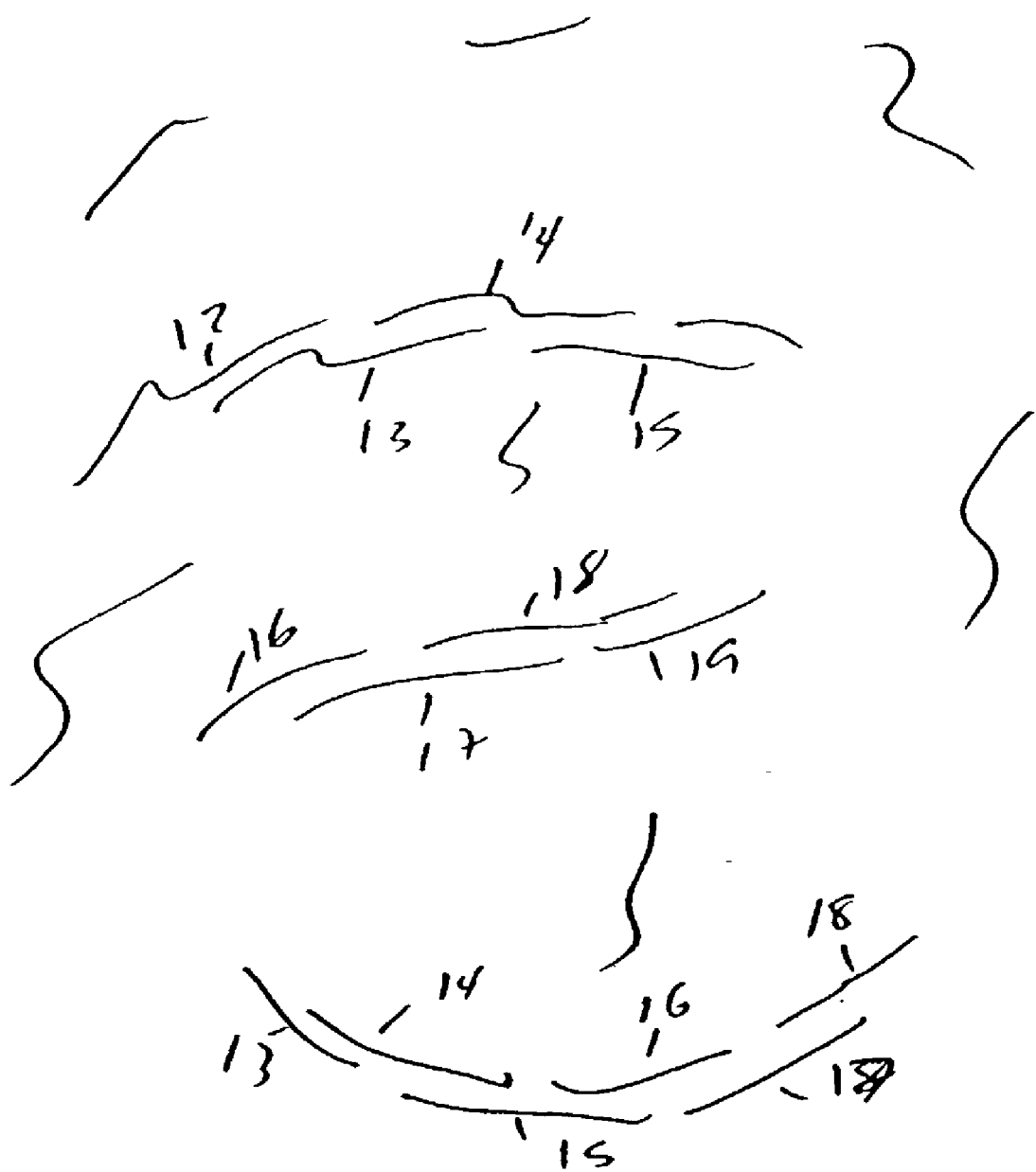
FIG. 3 illustrates conceptually how the DNA microarray of FIG. 2 is converted into a replication of the DNA molecule of FIG. 1.

The information about the sequence of the segments 12–19 is then used to construct a new totally fabricated DNA molecule. This process is initiated by constructing a microarray of single stranded DNA segments on a common substrate. This process is illustrated in FIG. 2. Each of the single stranded segments 12 through 19 is constructed in a single cell, or feature, of a DNA microarray indicated at 20. Each of the DNA segments is fabricated in situ in a corresponding feature indicated by reference numbers 22 through 29. Such a microarray is preferably constructed using a maskless array synthesizer (MAS), as for example of the type described in published PCT patent application WO99/42813 and in corresponding U.S. Pat. No. 6,375,903, the disclosure of each of which is herein incorporated by reference. Other examples are known of maskless instruments which can fabricate a custom DNA microarray in which each of the features in the array has a single stranded DNA molecule of desired sequence. The preferred type of instrument is the type shown in FIG. 5 of U.S. Pat. No. 6,375,903, based on the use of reflective optics. It is a desirable and useful advantage of this type of maskless array synthesizer in that the selection of the DNA sequences of the single stranded DNA segments is entirely under software control. Since the entire process of microarray synthesis can be accomplished in only a few hours, and since suitable software permits the desired DNA sequences to be altered at will, this class of device makes it possible to fabricate microarrays including DNA segments of different sequence every day or even multiple times per day on one instrument. The differences in DNA sequence of the DNA segments in the microarray can also be slight or dramatic, it makes no different to the process. The usual use of such microarrays is to perform hybridization test on biological samples to test for the presence or absence of defined nucleic acids in the biological samples. Here, a much different use for the microarray is contemplated.

The MAS instrument may be used in the form it would normally be used to make microarrays for hybridization experiments, but it may also be adapted to have features specifically adapted for this application. For example, it may be desirable to substitute a coherent light source, i.e. a laser, for the light source shown in FIG. 5 of the above-mentioned U.S. Pat. No. 6,375,903. If a laser is used as the light source, a beam expanded and scatter plate may be used after the laser to transform the narrow light beam from the laser into a broader light source to illuminate the micromirror arrays used in the maskless array synthesizer. It is also envisioned that changes may be made to the flow cell in which the microarray is synthesized. In particular, it is envisioned that the flow cell can be compartmentalized, with linear rows of array elements being in fluid communication with each other by a common fluid channel, but each channel being separated from adjacent channels associated with neighboring rows of array elements. During microarray synthesis, the channels all receive the same fluids at the same time. After the DNA segments are separated from the substrate, the channels serve to permit the DNA segments from the row of array elements to congregate with each other an begin to self-assemble by hybridization. This alternative will also be discussed further below.

Once the fabrication of the DNA microarray is completed, the single stranded DNA molecule segments on the microarray are then freed or eluted from the substrate on which they were constructed. The particular method used to free the single stranded DNA segments is not critical, several techniques being possible. The single stranded DNA molecules are suspended in a solution under conditions which favor the hybridization of single stranded DNA strands into double stranded DNA. Under these conditions, the single stranded DNA segments will automatically begin to assemble the desired larger complete DNA sequence. This occurs because, for example, the 3' half of the DNA segment 12 will either preferentially or exclusively hybridize to the complementary half of the DNA segment 13. This is because of the complementary nature of the sequences on the 3' half of the segment 12 and the sequence on the 5' half of the segment 13. The half of the segment 13 that did not hybridize to the segment 12 will then, in turn, hybridize to the 3' half of the segment 14. This process will continue spontaneously for all of the segments freed from the microarray substrate. By this process, a DNA assembly similar to that indicated in FIG. 1C is created. By joining the aligned single stranded DNA molecules to each other, as can be done with a DNA ligase, the DNA molecule 10 of FIG. 1A is completed. The number of copies of the molecule created will be proportional to the number of identical segments synthesized in each of the features in the microarray 20. It may also be desirable to assist the assembly of the completed DNA molecule be performing one of a number of types of sub-assembly reactions. Several alternatives for such reactions are described below.

There may need to be a purification and verification steps performed before and after assembly of the complete target DNA molecule. Since the DNA segments are built in a series of nucleotide addition reactions, and since no reactions are ever 100% complete, there may be some errors in the sequences of one or more DNA segments. Such erroneous segments will be released with the correct segments from the substrate and may have sufficient correct sequence to hybridize to another segment. Fortunately, most errors involve lack of nucleotide additions and therefore create segments that are too short. When the completed DNA segments are created, the shorter defective segments can be separated out and discarded first. The DNA molecules assembled from segments that are the correct design length should include the intended sequence. Verification of the intended sequence by sequencing may be needed, before or after the assembly of segments into larger DNA seuqences. The number of copies of the synthesized DNA can be increased by any the common techniques for that purpose, including PCR and replication of a plasmid in a competent host.

This process makes possible the direct fabrication of DNA of any desired sequence. No longer do expression vectors have to be constructed from component parts by techniques of in vitro recombinant DNA. Instead, any desired DNA construct can be directly synthesized in total by direct synthesis in segments followed by spontaneous assembly into the completed molecule. The constructed DNA molecule does not have to be one that previously existed, it can be a totally novel construct to suit a particular purpose. It now becomes possible for one of skill in the art to design a desired DNA sequence or vector entirely in the computer, and then to directly synthesize the DNA vector artificially in a single operation.

The size of DNA constructs which can be built in this manner is not particularly limited. Using a maskless array synthesizer, of the type shown in the previously mentioned U.S. Pat. No. 6,375,903, it has proven possible to construct microarrays having up to 700,000 oligonucleotide DNA segments, which can be 50 base pairs in length. Since the instrument permits the size of features in the microarrays to be under computer controls, the number of features can be altered as needed for the DNA to be constructed. Assume for the purposes of an example that only 200,000 separate DNA segments are created having a length of only 30 nucleotides. The finished double stranded DNA molecule that could be created using this example could be as long as 3 million base pairs. Since the maskless array synthesizer can create such a microarray in no more than 4 to 6 hours, it becomes possible to literally overnight produce any needed DNA construct of any reasonable size, from that a typical gene (1 to 20 kilobases), to that of a small genome (1 to 10 megabases). The direct fabrication of vectors for genetic engineering processes (typically 5 to 300 kb) can become a reality.

It is envisioned that the process of direct DNA synthesis envisioned here will begin with a desired target DNA sequence, in the form of a computer file representing the target sequence that the user wants to build. A computer software program is used to determine the optimal way to subdivide the desired DNA construct into smaller DNA that can be used to build the larger target sequence. The software would be optimized for this purpose. For example, the target DNA construct should be subdivided into segments in such a manner so that the hybridizing half of each segment will hybridize well to a corresponding half segment, and not to any other half segment. If needed, changes to the sequence not affecting the ultimate functionality of the DNA may be required in some instances to ensure unique segments. This sort of optimization is preferable done by computer systems designed for this purpose.

After the DNA segments are constructed on the substrate of the microarray, the DNA segments must be separated from the microarray substrate. This can be done by any of a number of techniques, depending on the technique used to attach the DNA segments to the substrate in the first place. Described below is one technique based on base labile chemistry, adapted from techniques used to fabricate oligonucleotides on glass particles, but this is only one example among several possibilities. In essence, all that is required is that the attachment of the DNA segments to the substrate be cleaved by a technique that does not destroy the DNA molecules themselves.

The DNA segment detachment method most preferred is method which will be referred to here as the safety-catch method. Under the safety-catch approach, the initial starting material for the DNA strand construction in the microarray is attached to the substrate using a linker that is stable under the conditions required for DNA strand synthesis in the MAS instrument conditions, but which can be rendered labile by appropriate chemical treatment. After array synthesis, the linker is first rendered labile and then cleaved to release the single stranded DNA segments. The preferred method of detachment for this approach is cleavage by light degradation of a photo-labile attachment group. Described below in the examples is an embodiment of a safety-catch linker which is stable under the condition of DNA strand synthesis in an MAS instrument, but which can be treated with an activator (trifluoroacetic acid) to render the linker photo-labile. An advantage of the use of the safety-catch approach is that the linkage is stable during DNA synthesis conditions, but then becomes photo-labile after activation. Once the linkage is rendered photo-labile, while the microarray is still in the MAS instrument, the light source and micromirrors can be used to selectively detach the DNA segments from the substrate. The DNA segments can thus be freed from the substrates in groups of segments from selected features of the microarray, to facilitate proper hybridization and assembly of the desired DNA construct. For example, referring again to the simplified schematic of FIG. 1, it would be possible to selectively detach only DNA segments 12 and 13 from the substrate, leaving all the other segments tethered, until sufficient time has passed to permit proper hybridization between strands 12 and 13.

A significant advantage of this safety-catch approach is that DNA segments are released from the substrate only when desired. Thus DNA segments formed in the "lanes" between features are not released, and another source of possible error is avoided. The selective release of DNA segments from the substrate allows for the staging of the release of those segments into solution to thus providing some order to the assembly of segments into larger DNA assemblies. This staging can be manipulated in order to facilitate correct DNA sequence assembly.

Permitting the DNA segments freed from the microarray to synthesize the complete DNA molecule presents no particular difficulty to those who work with DNA. For example, at 94° C. DNA molecules will relax and become single stranded. By slowly cooling to 4° C., the DNA molecules in a solution will find their complementary sequences and hybridize to them if possible. A DNA ligase may be used to close any nicks remaining in the double stranded DNA molecule created by the hybridization process.

Another interesting application for this process is to permit the use of DNA constructs of any desired sequence at any desired location. Consider the problem of supplying DNA vectors or constructs to a physically remote location, such as an Antarctic research station or to a space station. Instead of sending DNA molecules, imagine instead that the remote location is supplied with a maskless array synthesizer and a supply of the necessary reagents. Then the information as to what DNA molecules are needed can be sent to the remote location by radio transmission, and the needed DNA can be directly synthesized on location. In essence, the DNA has been faxed to the remote location in much the same way that a document can be faxed from one location to another. Really electronic information is transmitted from one location to another and that information is used to create the facsimile copy of the original. In this case the copy is made in DNA.

Uses of this process include making expression vectors for any hosts, probes for testing or diagnosis, DNA vaccines, DNA constructs with codon usage adapted for expression in a particular host, and DNA for any other purpose whatsoever. Since this process is entirely independent of the sequence of the synthesized DNA, any needed functional DNA components for which sequence is known can be built into the construct, including promoters, protein coding regions, terminators, transcriptional elements, origins of replication or encapsulation, recognition sites for restriction enzymes, or any other useful functional DNA segments.

This process may or may not make enough directly synthesized DNA as needed for a particular application. It is envisioned that more copies of the synthesized DNA can be made by any of the several ways in which other DNA constructs are cloned or replicated in quantity. An origin of replication can be built into circular DNA which would permit the rapid amplification of copies of the constructed DNA in a bacterial host. Linear DNA can be constructed with defined DNA primers at each end which can then be used to amplify many copies of the DNA construct by the PCR process.

One interesting application of this process would be a kind of combinatorial approach to DNA mutation. If one segment of the total DNA construct is made in several or many features, each of which makes a segment of slightly different sequence, a collection of DNA constructs can be made which vary in sequence at one or more locations. This process can be used to make site directed random DNA mutations for testing variations in DNA or protein sequence for a desired application. This approach can also be used to make a population of expression vectors which have variations in the proteins they encode. The expression vectors can then be transformed into hosts and the expressed proteins screened for the desired biological activity.

It is understood that the invention is not confined to the particular embodiments set forth herein as illustrative, but embraces all such modified forms thereof as come within the scope of the following claims.

EXAMPLES

Prophetic

General Protocol for the Synthesis of Double Stranded DNA Sequences

Synthesis of Protected Diamine Linker and Photolabile Nucleotide Succinates

Figure 4:
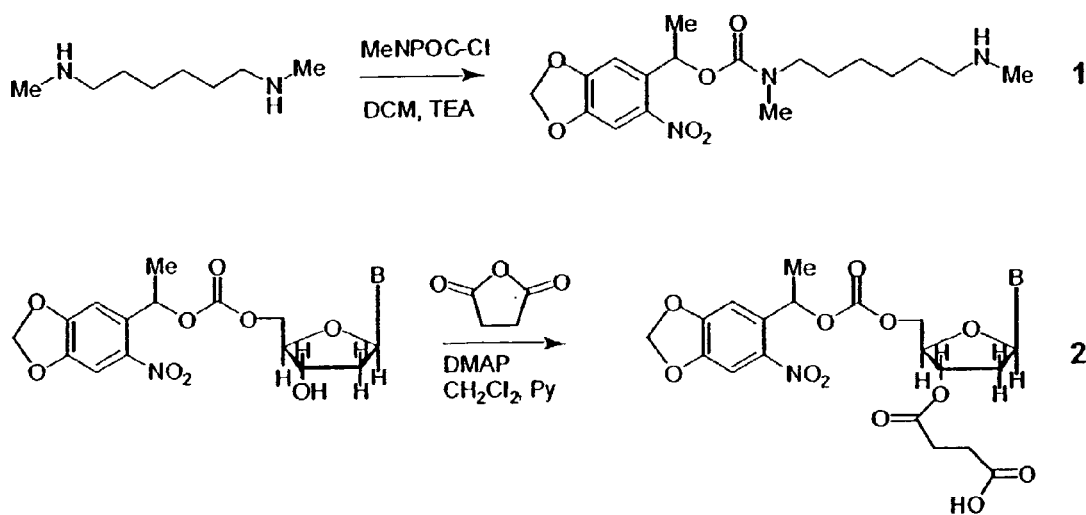
FIG. 4 illustrates an exemplary base labile chemistry for use in the present invention.

The mono MeNOPC protected diamine is illustrated as compound 1 in scheme 1 in FIG. 4. The 5-MeNPOC, 3'-OH-nucleotides with appropriately protected bases is described by McGall et al., Jour. Amer. Chem. Soc. 119, 5081–5090 (1997) are each converted to their 3-succinates (represented by structure 2 in scheme 1, FIG. 4) by treatment with succinic anhydride and dimethylaminopyridine (DMAP) in dichloromethane/pyridine solution.

Preparation of Slides and Oligonucleotide Synthesis (Base Labile Linker)

Figure 5:
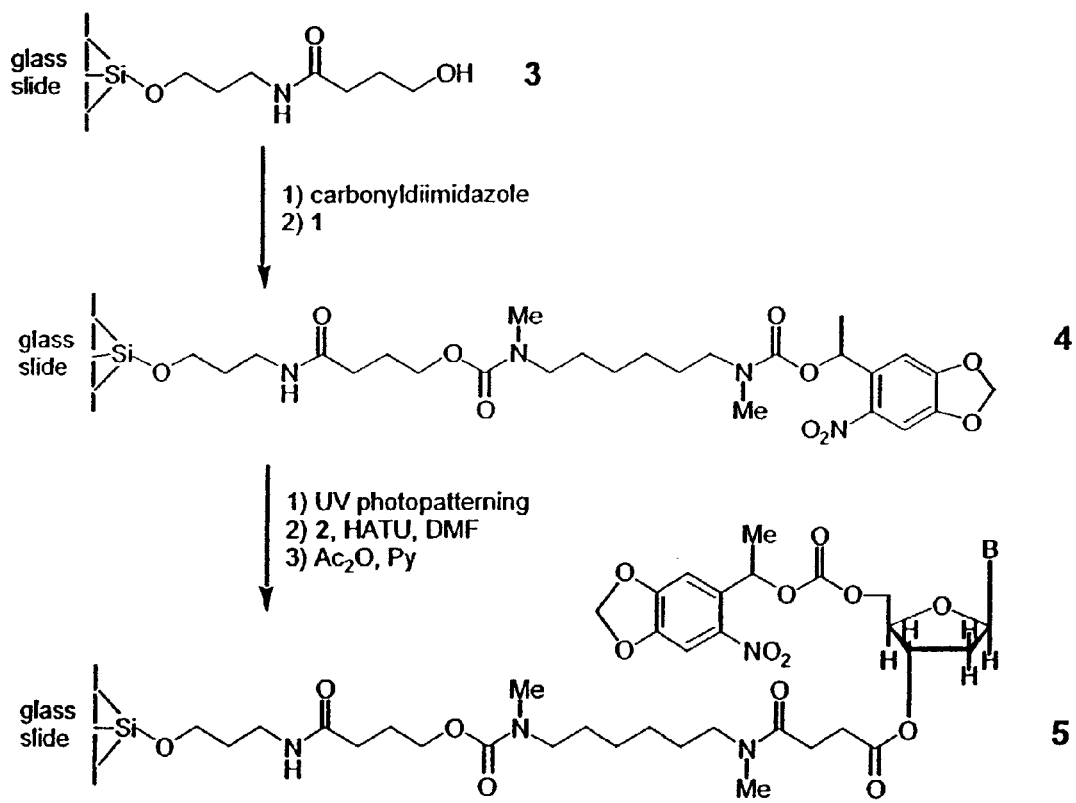
FIG. 5 illustrates an exemplary surface chemistry which may be used in the present invention.

Microscope slides are prepared as described by Singh-Gasson et. al, Nature Biotechnology 17, 974–978 (1999) yielding a glass surface derivatized with a linker bearing a free alcohol at the terminus, depicted as structure 3 in scheme 2, FIG. 5). This slide is soaked in an 0.6 M solution of carbonyldiimidazole in dry dichloromethane (6 hours), washed with dry dichloromethane, followed by soaking in a solution MeNPOC-protected diamine (compound 1, scheme 1) (0.4 M) for 12 hours. The slide is then washed with dichloromethane to yield surfaces with secondary amines capped by the photolabile protecting group MeNPOC (structure 4 scheme 2). In the first 4 cycles of synthesis, the maskless array synthesizer will photo-deprotect the secondary amines in the appropriate array elements for attachment of each of the protected nucleotide-3'-succinates with the coupling reagent O-Benzotriazole-N,N,N'N'-tetramethyluronium-hexafluoro-phosphate (HBTU) in DMF. Unreacted free amines are subsequently capped with acetic anhydride in pyridine. Once the 3'-nucleotides have been attached to the surface subsequent deprotection and elongation cycles are conducted as described in Singh-Gasson et. al. Nature Biotechnology, 17, 974–978 (1999) and as also described in. Published PCT patent application WO99/42813.

Gene Synthesis

In this example, the maskless array synthesizer is used to conduct the synthesis of oligonucleotide fragments on a glass slide. Following release of the oligonucleotide fragments from the slide, the fragments will be assembled into a long double stranded DNA of defined sequence by self assembly and the polymerase chain reaction (PCR), ligase chain reaction (LCR) or both.

Figure 6:
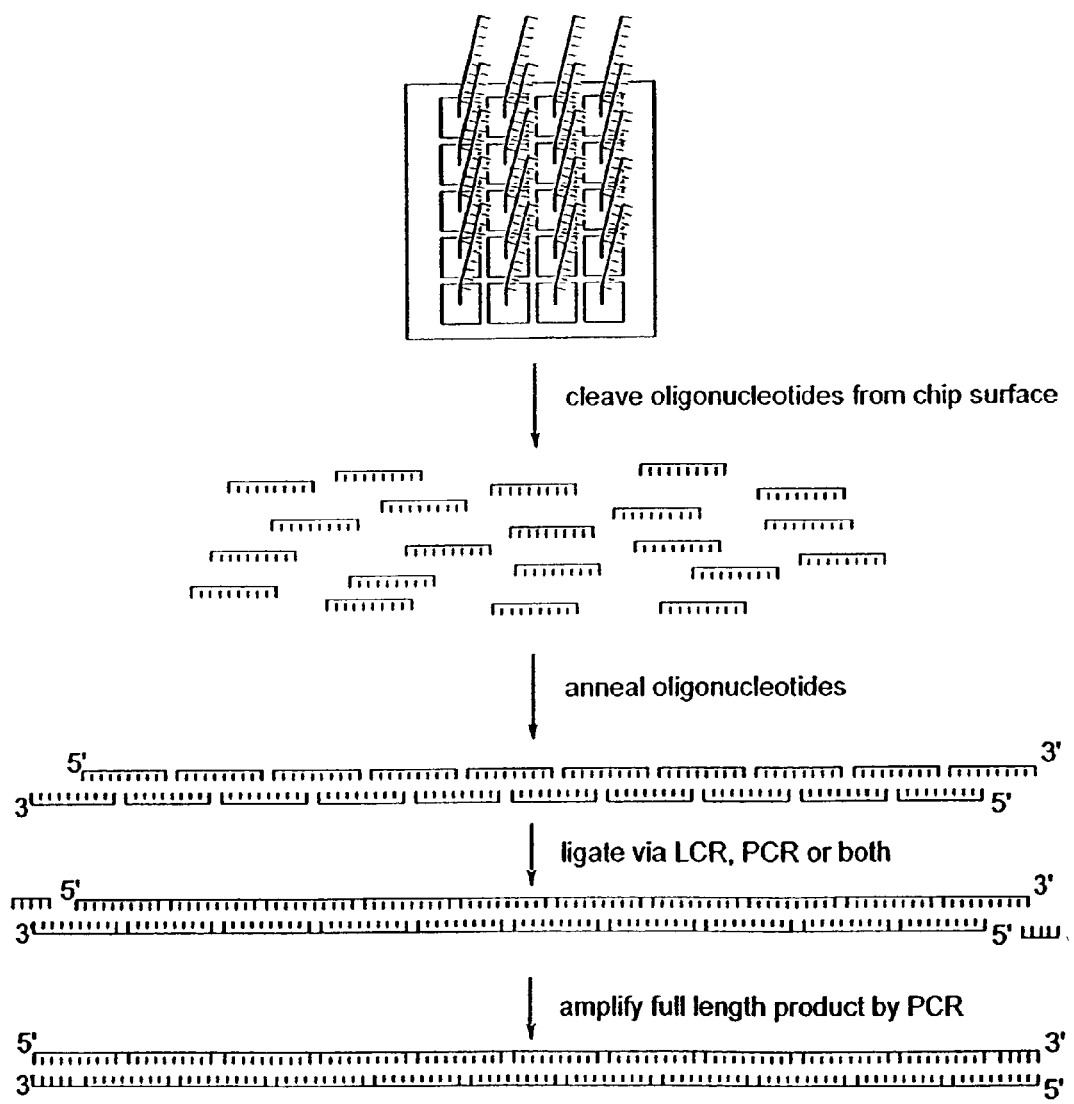
FIG. 6 illustrates the process of sequence assembly in the present invention.

For the purpose of this example we consider the synthesis of a double stranded DNA fragment of 420 base pairs in length, of an arbitrary but defined sequence. The target sequence is divided into 20 overlapping 40-mer oligonucleotides. Of the 20 oligonucleotides or segments, 10 are designated for each strand of the target sequence, and the segments are designed to that that they can self assemble into the full length sequence by virtue of the 3'-overhangs of 20 bases on either strand (FIG. 6). Software is used to select virtual oligonucleotides from the target sequence and to divide the available array element on the chip evenly for the synthesis of the 20 oligonucleotide fragments. After the synthesis is completed as described above, the slide is incubated with a minimal volume of concentrated ammonium hydroxide and heated to 55° C. for 4 hours, to cleave the oligonucleotides from the surface of the slide and to remove all protecting groups from the bases. The solution is concentrated to dryness in a Speedvac, redissolved in 50 uL of T4 polynucleotide kinase buffer (Promega) and the 5'-hydroxyls of the oligonucleotides are phosphorylated with 20 U of T4-polynucleotide kinase (Promega) at 37° C. for 2 hours. The resulting mixture of phosphorylated oligonucleotides is separated by size on an 8% denaturing polyacrylamide gel electrophoresis. The band corresponding to the full length 40 mer oligonucleotides is excised from the gel and the mixture of oligonucleotides is purified from the gel by freeze/thaw and elution (detailed protocols for each of these procedures can be found in Short Protocols in Molecular Biology 4th edition F. M. Ausubel et. al. Eds. 1999). The purified oligonucleotides are dissolved in LCR buffer (Stratagene) containing 8 U of Pfu DNA ligase (Stratagene). The result of that process is that the individual oligonucleotides are annealed and ligated together to produce a full length DNA sequence by thermal cycling (94° C.-1 min; 40 cycles of: 55° C. for 90 sec, 70° C. for 90 sec, 95° C. for 30 sec; 55° C. for 2 min, 72° C. for 2 min). The full-length oligonucleotide is subsequently amplified by PCR using standard protocols from the LCR reaction using 2 20-mer oligonucleotide primers that are complementary to the 3' overhangs in this example.

The above detailed description of a gene synthesis protocol is provided as an example for practicing the invention. There are many possible variations on this protocol using LCR, PCR or both to anneal and amplify the oligonucleotides into a longer double stranded DNA sequence (Kneidinger et al., Bio Techniques, 30, 248–249 (2001); Withers-Martinez et al., Protein Eng. 12, 1113–1120 (1999); Casimiro et al., Structure (London), 5, 1407–1412 (1997); Holowachuk et al., PCR Methods Appl. 1995, 4, 299–302 (1995); Prodromou et al., Protein Eng. 5, 827–829 (1992); Engels, Angew. Chem., 101, 733–52 (1989)). The precise details of this protocol can be altered by a practitioner skilled in the art to optimize the efficiency of the process in a variety of obvious ways such as altering the linker chemistry, the length of the oligonucleotides, the codon usage in each oligonucleotide and thus the hybridization properties of the sequences, the number of oligonucleotides used for construction of each segment, the conditions of the LCR and/or PCR assembly reactions etc. The DNA segments need not be all of the same length, but can be of any desired length within the limits of the quality of segments that can be produced by a given instrument with particular chemistry.

Channels.

Figure 7:
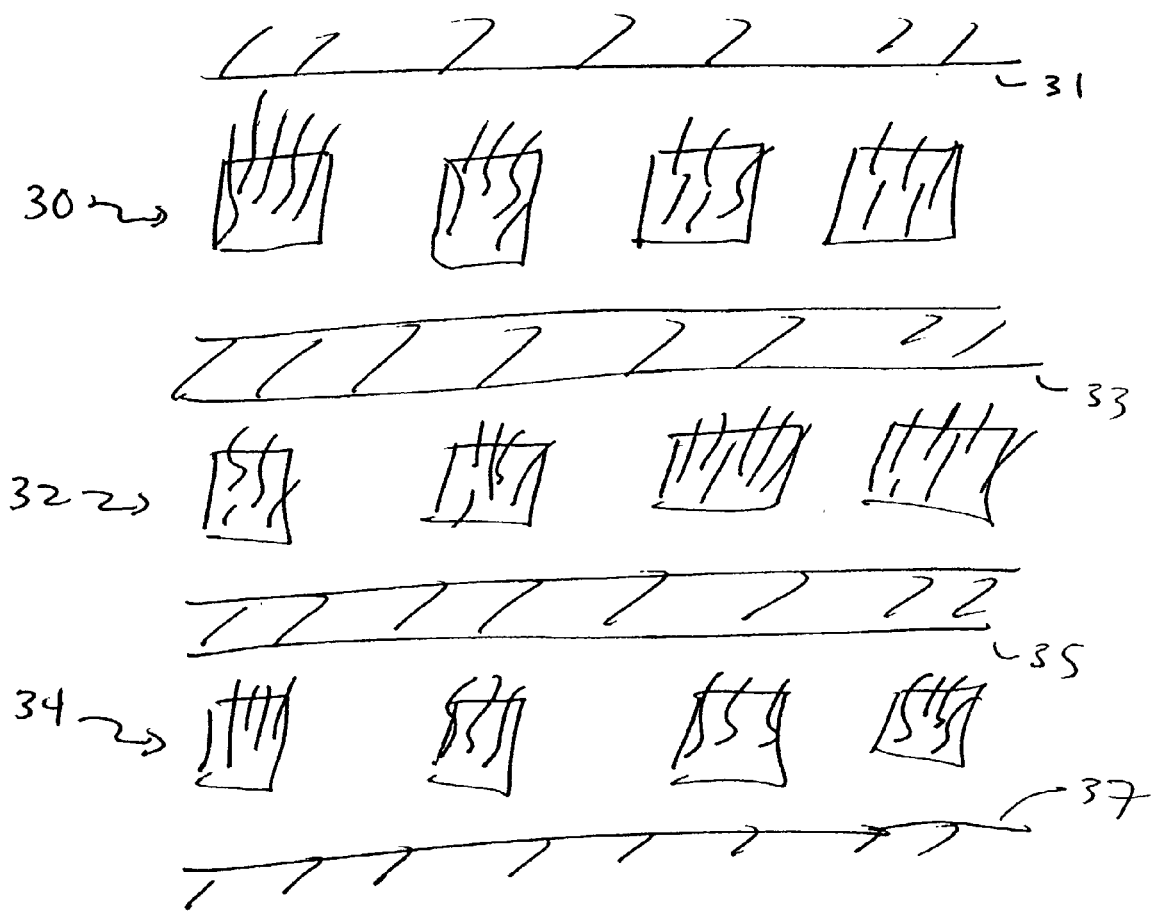
FIG. 7 illustrates a variation in the practice of the present invention.

As mentioned above, it is also envisioned that the flow cell in the MAS instrument can be provided with channels. FIG. 7 illustrates this concept. In FIG. 7, the microarray is designed so that the cells or features of the array are aligned in linear rows, designated 30, 32 and 34, which are spaced physically from each other. The flow cell then includes physical separators, designated 31, 33, 35 and 37 in FIG. 7 to separate the rows from each other. This construction thus forms linear channels in which fluids may flow, the channels being separated from each other. The channels may be all connected to each other at their common ends to permit introduction of reagents and media into the flow cells for microarray synthesis procedures. The advantage of this arrangement is only evident after synthesis of the DNA segments. Whether the DNA segments made on the microarray are released from the substrate selectively or in unison, the DNA segments in the channel above row 32 are only able to hybridize to the on the DNA segments in that same channel, and the same is true for the DNA segments in each of the other channels. Since the DNA segments can be arranged on the microarray under software control, it could seen logical to make adjoining DNA segments in cells of the array in the same channel. Then the DNA segments, once released, would assemble into larger DNA segments, which may be thought of as DNA sub-assemblies. Only after the DNA sub-assemblies have been formed are the sub-assemblies brought together to hybridize to make the completed DNA target molecule. Kinases, ligases and/or polymerases may be added as needed to complete the assembly of the DNA molecule. This approach not only minimizes the time needed to obtain complete assembly of larger DNA molecules, it minimizes any possible hybridization mismatches since similar sequences in distant regions of the target DNA molecule are not permitted to be exposed to each other until after those similar regions have been hybridized to the sequences to which they are supposed to hybridize with.

Safety Catch Chemistry

Figure 8:
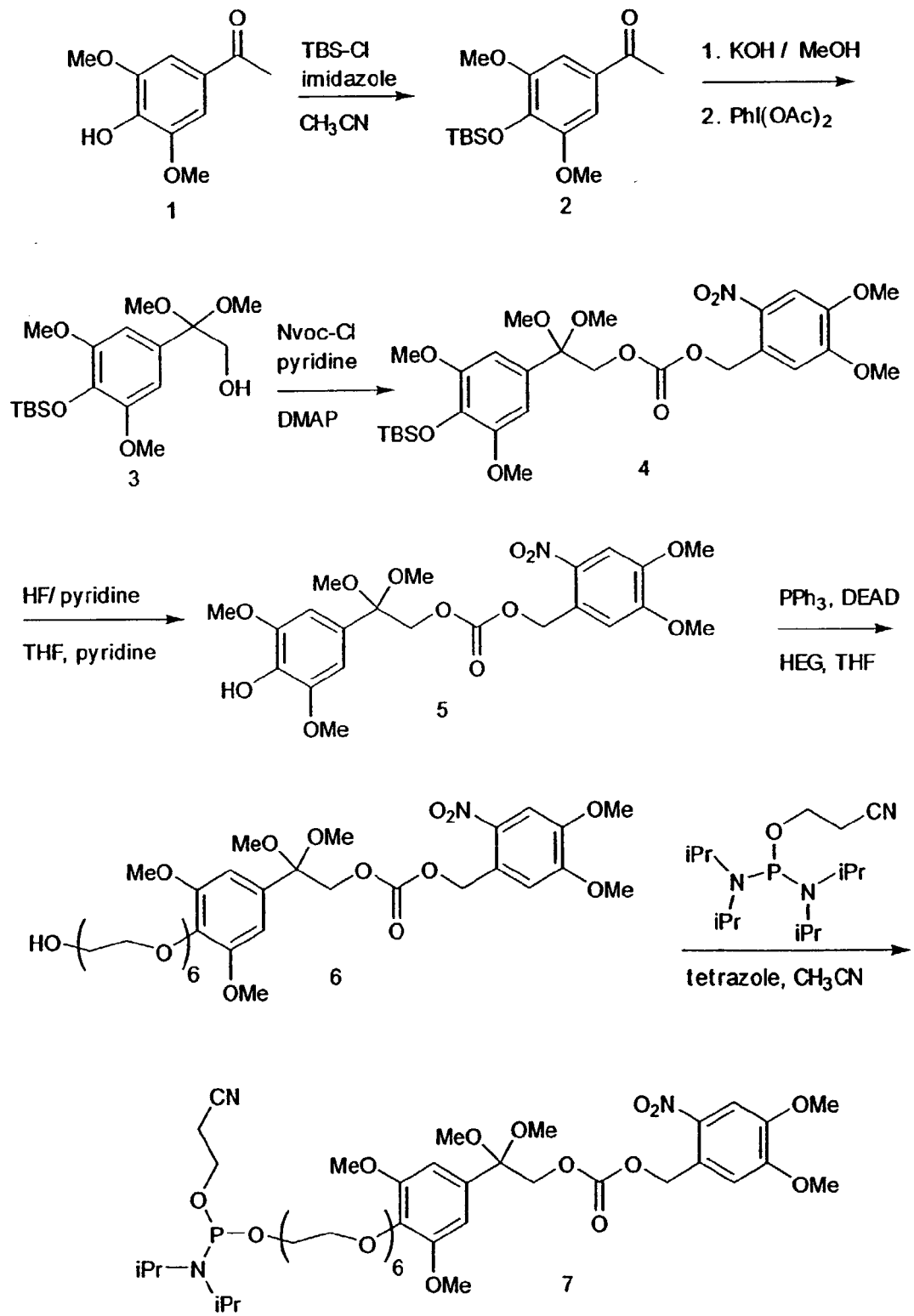
FIGS. 8 and 9 illustrate the chemistry of another method of making a labile connection of DNA segments to a substrate.
Figure 9:
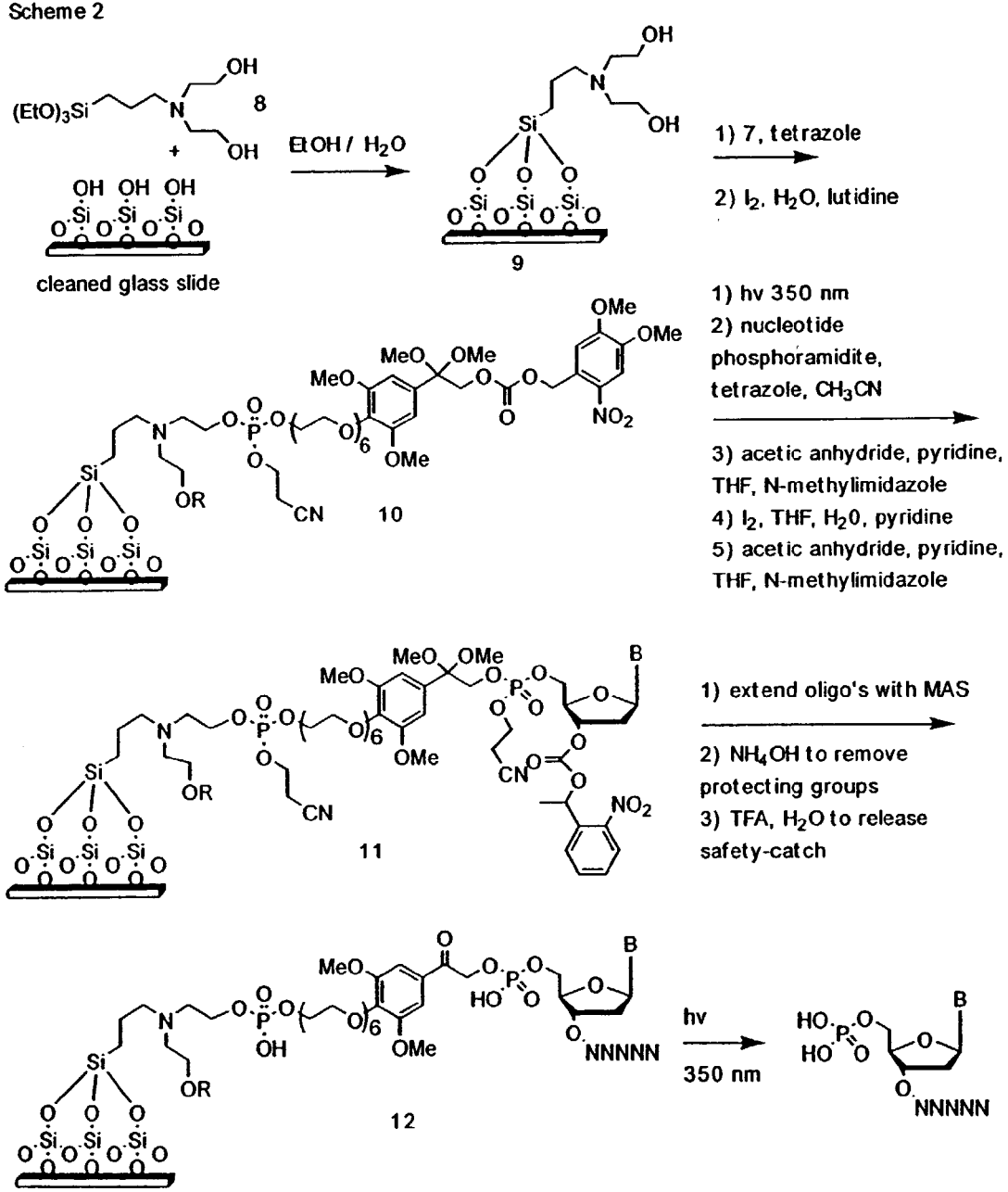

Shown in FIGS. 8 and 9 are details of exemplary safety-catch chemistry. Beginning in FIG. 8 with scheme 1, the synthesis of compound 3 is done with modifications to the protocol of Luis and Andrés, Synthesis of Danielone (a-Hydroxyacetosyringone), *J. Chem. Research (S)*, 1999, pp. 220–221. Starting with the commercially available compound 1,3',5'-Dimethoxy-4'-hydroxyacetophenone, the phenol is protected with the TBS protecting group. Compound 1, and an excess of imidazole and TBS-Cl are dissolved in dry acetonitrile, and the reaction mixture is stirred under a nitrogen atmosphere. Upon completion, the crude material is purified by column chromatography, followed by recrystalization to give compound 2. Compound 3 is then obtained by forming the enolate of compound 2 with KOH in methanol, followed by addition of iodobenzene diacetate in accordance with the method of Moriarty and Hou, "a-Hydroxylation of Ketone Using o-Iodosylbenzoic Acid" *Tet. Lt.* 1984, pp. 691–694 to afford, after column chromatography and recrystalization, pure compound 3.

The photocleavable Nvoc group is then appended onto compound 3 according to the procedure developed by McGall, et al., "The Efficiency of Light Directed Synthesis of DNA Arrays on Glass Substrates" *JACS* 1997, pp. 5081–5090. Compound 3 is dissolved in anhydrous pyridine, under an inert atmosphere of nitrogen, and then cooled to −15° C. To this is added a solution of Nvoc-C1 and catalytic DMAP in dry methylene chloride. After 30 minutes the reaction is warmed to room temperature, and left to stir overnight. Work up, followed by column chromatography and recrystalization yields pure compound 4.

The phenolic TBS is deprotected (Greene, T. W. and Wuts, P. G. M. *Protective Groups in Organic Synthesis*, 3rd ed. John Wiley & Sons, Inc. New York. 1999, p 134) using a buffered hydrogen fluoride/pyridine stock solution in tetrahydrofuran (THF) prepared according to the procedure of Trost et al., "Sulfur-Substituted Dienes and the Silyene Protecting Group in Synthesis. Deoxypillaromycinone" *J. Org. Chem.* 1983, pp. 3252–326. Compound 4 is dissolved in a solution of 10% pyridine in THF. To this is added an equal volume of the buffered hydrogen fluoride/pyridine stock solution, and the reaction was stirred at room temperature for 1.5 hours. Column chromatography, followed by recrystalization yields pure compound 5.

A standard Mitsunobo reaction is then used to couple compound 5 with hexa(ethylene glycol) (HEG), Benfaremo, et al. "Synthesis and Characterization of Luminescent Polymers of Distyrylbenzenes with Oligo(ethylene glycol) Spacers" *Macromolecules* 1998, pp. 3595–3599. To a dry flask is added the HEG, triphenylphosphine, and compound 5 under an inert atmosphere. These are then dissolved in dry THF, followed by dropwise addition of diethyl azodicarboxylate (DEAD). The reaction is then heated to 45° C. and stirred for three days with periodic addition of more DEAD. Compound 6 is isolated by column chromatography.

Phosphitylation of compound 6 is accomplished using the procedure of Barone, et al., *Nucleic Acids Res.* 1984, pp. 4051–4061. An excess of 2-cyanoethyl-N,N,N',N'-tetraisopropylphosphorodiamidite, compound 7, and catalytic diisopropylammonium tetrazolide in dry acetonitrile are stirred for 24 hours under anhydrous conditions. Purification by column chromatography yields pure phosphoramidite 7.

Glass slides are cleaned and derivatized according to the procedure of McGall and Fidanza, "Photolitographic Synthesis of High-Density Oligonucleotide Arrays" *Methods in Mol. Bio. Vol.* 170, pp71–101 (illustrated in Scheme 2, FIG. 9). Slides are cleaned by soaking them successively in peroxysulfuric acid (Nanostrip) for 15 minutes, followed by 10% aq. NaOH at 70° C. for 3 min., and then with 1% aqueous HCl (1 min.), rinsing with deionized water between each step. The slides are spun dry under nitrogen, and then agitated in a 1% solution of N,N-bis(2-hydroxyethyl)-3-aminopropyltriethoxysilane in 95:5 EtOH/H2O to yield surface 9.

The next subsequent steps of chemical processing are performed using the DNA synthesizer which is pare of the maskless array synthesizer (MAS), and these steps are again illustrated in FIG. 9, scheme 2. The linker is coupled onto surface 9 with tetrazole, followed by capping with acetic anhydride and a standard iodine oxidation cycle to give the composition indicated at 10 in FIG. 9.

Photodeprotection of composition 10 with the MAS instrument, coupling of a suitably protected 3'-NPPOC-nucleoside-5'-phosphoramidite with tetrazole, capping, oxidation and capping gives the composition indicated at 11 in FIG. 9. In composition 11, the B indicates the nucleoside side member of the first base pair in the DNA segment sequence, i.e. A, T, C or G. This cycle of photodeprotection, coupling, capping, oxidation and capping is repeated with the desired nucleotide phosphoramidites to extend the DNA segments built on the substrate to the desired length with the MAS to make the composition indicated at 12. In composition 12, the NNNNN indicates the location of the following nucleotides added to the DNA segment. Following oligonucleotide extension, also termed here as DNA segment synthesis, removal of the nucleobase and phosphodiester protecting groups is accomplished by treatment with aqueous ammonium hydroxide. This process removes the CN protecting groups from 11. Removal of the safety-catch protecting group (hydrolysis of the dimethyl ketal) is done with 1% aqueous trifluoroacetic acid as indicated at 12 in FIG. 9. to remove the two methyl groups adjacent to the second phosphoester. Light directed cleavage of arrangement 12 directly releases the 5'-phosphorylated DNA segments from the surface of the substrate and into solution.

It should be noted that the scheme illustrated in FIG. 9 only shows the synthesis of one oligonucleotide per attachment site to the glass slide and the second oligonucleotide is represented as R. In addition the chemistry is outlined for the synthesis of oligonucleotides in the 5'-3' direction allowing the direct release of 5'-phosphorylated oligonucleotides. Equivalent protocols can be used for the synthesis of oligonucleotides in the 3'–5' direction with the release of 3' phosphorylated oligonucleotides that can be converted after release to 5' phosphorylated oligonucleotides (with T4-polynucleotide kinase and ATP) prior to assembly of the oligonucleotides into larger DNA fragments. See, for example Beier and Hoheisel, *Journ. Biotech.,* 94:15–22 (2002). Additionally, many variations are possible in the structure of the safety-catch photocleavable linker (the dimethoxy ketal linkage in composition 10) that produce a functionally equivalent linker. For example, the substitution of the aromatic ring (R2) can be altered, the dimethoxy ketal safety-catch can be substituted with a variety of other acid labile ketals (R1) and the NVOC group can be readily substituted with another photocleavable protecting group (PCPG) and thus the linker is best represented by the following compound:

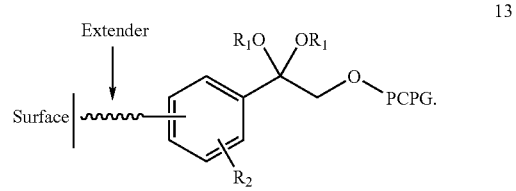

13

We claim:

1. A method for the fabrication of a DNA construct of a target sequence comprising the steps of
   (a) defining a plurality of overlapping single stranded DNA sequence segments which in the aggregate would make up the target DNA sequence, wherein the single stranded segments overlap in the regions where the segments are complementary to each other;
   (b) making a DNA microarray on a substrate, the microarray made up of features having single stranded DNA molecules, the single stranded DNA molecules selected to be overlapping sequence segments of the target sequence, the single stranded DNA molecules being made attached by linkers to the substrate, the linkers being stable under the conditions of DNA synthesis for the microarray, the linkers also being capable of being rendered photo-labile by chemical treatment;

(c) detaching the single stranded DNA molecules from the substrate by first applying a chemical modification to the linkers to render the linkers light labile and then by selectively applying light to cleave the labile linkers in areas of single stranded DNA molecules thus detaching the single stranded DNA molecules from the substrate; and (d) allowing the single stranded DNA molecules detached in step (c) to assemble into a double stranded target DNA construct by providing conditions favoring hybridization of the single stranded DNA molecules to each other using the 3' overhang contained on either strand.

2. The method as claimed in claim 1 wherein the step of defining the overlapping sequence segments is a logical not a physical step performed by computer.

3. The method as claimed in claim 1 wherein the step of making a DNA microarray is performed using a maskless array synthesizer instrument.

4. The method as claimed in claim 1 wherein the step of allowing the segments to assemble includes cooling the DNA segments under conditions favoring hybridization of DNA segments.

5. The method as claimed in claim 1 wherein the step of assembling the DNA segments also includes the use of a DNA ligase, a DNA polymerase, or a DNA kinase.

6. A method for the fabrication of a target DNA construct of comprising the steps of (a) defining a plurality of overlapping single stranded DNA sequence segments which in the aggregate make up the target DNA construct, wherein the single stranded segments overlap in the regions where the segments are complementary to each other;

(b) making the single stranded DNA molecules in an array on a substrate, the single stranded DNA molecules linked to the substrate by base labile linkers;

(c) releasing the single stranded DNA molecules from the substrate by alkaline treatment of the array to cause the base labile linkers to release the single stranded DNA molecules; and (d) allowing the single stranded DNA molecules to assemble into a double stranded target DNA construct by providing conditions favoring hybridization of the single stranded DNA molecules to each other using the 3' overhang contained on either strand.

7. The method of claim 1 wherein some of the DNA molecules that are detached are physically separated from others of the detached DNA molecules so that hybridization of desired DNA sub-assemblies is permitted while incorrect assemblies are inhibited.

8. The method of claim 6 wherein the step of allowing the DNA molecules to assemble also includes the addition of a DNA ligase, a DNA polymerase or a DNA kinase.

9. A method for the fabrication of a DNA construct of a target sequence comprising the steps of (a) defining a plurality of overlapping single stranded DNA sequence segments which in the aggregate would make up the target DNA sequence, wherein the single stranded segments overlap in the regions where the segments are complementary to each other;

(b) making a DNA microarray on a substrate in which single stranded DNA molecules constructed in the microarray are the overlapping sequence segments, the DNA molecules each being attached to the substrate by a linker which is stable while the microarray is being made, the linker being capable of being rendered photo-labile by chemical treatment;

(c) releasing the single stranded DNA molecules from the substrate by chemical treatment to modify the linkers to become light labile and then using light to cleave the linkers to release the single stranded DNA molecules;

(d) allowing the single stranded DNA molecules released in step (c) to assemble into a double stranded target DNA construct by providing conditions favoring hybridization of the single stranded DNA molecules to each other using the 3' overhang contained on either strand; and (e) ligating said assembled DNA molecules into a DNA molecule of the target sequence.

* * * * *

UNITED STATES PATENT AND TRADEMARK OFFICE
CERTIFICATE OF CORRECTION

| | | |
|---|---|---|
| PATENT NO. | : 7,183,406 B2 | Page 1 of 1 |
| APPLICATION NO. | : 10/152046 | |
| DATED | : February 27, 2007 | |
| INVENTOR(S) | : Peter J. Belshaw et al. | |

It is certified that error appears in the above-identified patent and that said Letters Patent is hereby corrected as shown below:

Column 1 insert

STATEMENT REGARDING FEDERALLY SPONSORED RESEARCH OR DEVELOPMENT

This invention was made with United States government support awarded by the following agency:

DOD ARPA N39998-01-2-7070

The United States has certain rights in this invention.

Signed and Sealed this

Fifteenth Day of May, 2007

JON W. DUDAS
*Director of the United States Patent and Trademark Office*